United States Patent [19]

Maurer et al.

[11] Patent Number: 4,867,963
[45] Date of Patent: Sep. 19, 1989

[54] ENHANCEMENT OF NMR IMAGING OF TISSUE BY PARAMAGNETIC PYROPHOSPHATE CONTRAST AGENT

[75] Inventors: Alan H. Maurer, Wynnewood, Pa.; Linda C. Knight, East Windsor, N.J.; Jeffrey A. Siegel, Voorhees, N.J.

[73] Assignee: Temple University of the Commonwealth System of Higher Education, Philadelphia, Pa.

[21] Appl. No.: 008,674

[22] Filed: Jan. 29, 1987

[51] Int. Cl.$^4$ ............................................. A61K 49/00
[52] U.S. Cl. ...................................... 424/9; 424/603; 128/653; 128/654; 436/173; 436/806
[58] Field of Search .................... 128/653, 654; 424/9, 424/128; 436/173, 800

[56] References Cited

U.S. PATENT DOCUMENTS 4,615,879 10/1986 Runge et al. ......................... 436/806
4,647,447 3/1987 Gries et al. ............................. 424/9

OTHER PUBLICATIONS

McNamara, M.D. et al., Radiology, vol. No. 158, 765–769, 1986.
Wesby, M.D. et al., Radiology, vol. No. 153, 165–169, 1984.
McNamara, M.D. et al., Radiology, vol. No. 153, 157–163, 1984.
Tscholakoff, M.D. et al., Radiology, vol. No. 160, 515–519, 1986.
Buja, M.D. et al., J. Clin. Inv. vol. No. 57, 1508–1522, 1976.
Buja, M.D. et al., Circulation, vol. No. 52, 596–607, 1975.
Bianco et al., Clinical Sciences, vol. No. 24, 485–491, 1983.

*Primary Examiner*—Robert J. Warden
*Assistant Examiner*—Robert Benson
*Attorney, Agent, or Firm*—Seidel, Gonda, Lavorgna & Monaco

[57] ABSTRACT

Nuclear magnetic resonance imaging of animal or human tissue is enhanced when a paramagnetic pyrophosphate compound is administered intraveneously as a contrast agent. The contrast agent is particularly useful in magnetic resonance imaging of area of tissue calcification, such as acute myocardial infarctions. Specific localization of paramagnetic pyrophosphate in ischemic and necrotic muscle cells at the periphery of a myocardial infarction makes accurate localization and sizing of the central infarct and peri-infarct zones possible.

18 Claims, No Drawings

ENHANCEMENT OF NMR IMAGING OF TISSUE BY PARAMAGNETIC PYROPHOSPHATE CONTRAST AGENT

Reference to Government Grant

The invention described herein was supported by National Institutes of Health Biomedical Research Support Grant (BSRG) #RR05417.

FIELD OF THE INVENTION

This invention relates to an improvement in magnetic resonance imaging in animals and humans. The invention relates in particular, to the specific localization of a paramagnetic pyrophosphate compound in ischemic and necrotic muscle cells at the periphery of a myocardial infarct, making localization and sizing of the infarction possible.

BACKGROUND OF THE INVENTION

The diagnosis of acute myocardial infarction may be made with the typical clinical findings of chest pain, coupled with sequential electrocardiographic changes. Biochemical laboratory tests relying on measurement of the release of creatine kinase (CK) or the CK-MB and CK-B myocardial injury and the size of the infarction. In many clinical cases the diagnosis can be made with good certainty. However, these traditional techniques are limited. Frequently it is not possible to determine whether an episode of ischemia has resulted in tissue damage.

The location and extent of damage to muscle in acute myocardial infarction are important determinants of patient prognosis. Determination of the infarct area is of clinical importance, especially with the development of newer therapeutic methods to limit infarct size.

D'Agostino first showed that calcium complexes will localize in necrotic myocardial cells. *Am J. Pathol.* 45:633 (1964). It is believed that phosphorus compounds such as pyrophosphate enter the damaged cell under anaerobic conditions to bind apatite-like calcium crystals. Tissue calcium in ischemically-injured myocardial cells increases in dense bodies within the mitochondria. Bonte et al first proposed that a pyrophosphate compound that would bind intracellular calcium could be used to image acute myocardial infarctions. *Radiology* 110: 473 (1974). Over ten years of experience with animal and clinical studies in man have confirmed the ability of technetium-99m labelled pyrophosphate to detect and size acute myocardial infarctions.

Animal studies have confirmed that technetium-99m labeled pyrophosphate localizes predominantly in areas of intact perfusion in the outer peripheral region of infarcts in tissue characterized by muscle cell calcification. Buja et al, *J. Clin. Invest.* 57: 1508–1522 (1976); *Circulation* 52: 546–607 (1975). This preferential localization in the border zone of an area of infarction permits better definition of the central area of necrosis in a pattern often described as the "donut" sign. Further studies have confirmed that pyrophosphate can also localize in peripheral ischemic, but not infarcted, myocardium. Bianco et al, *J. Nucl Med.* 24: 485–491 (1983). This ability to localize in the ischemic "area at risk" of infarction is a unique property of pyrophosphate which may be useful for evaluating newer drug interventions for limiting the infarct size.

The use of Tc-99m radiolabeled pyrophosphate has constituted an advance in the ability to detect and localize acute myocardial infarctions. However, the inherent low spatial resolution of nuclear medicine imaging devices limits this technique's usefulness particularly in diagnosing small subendocardial infarcts. Recent work has confirmed the need for better spatial resolution as the use of newer tomographic nuclear medicine cameras has resulted in improved diagnostic ability especially for small areas of infarction. In general, however, because of the limited spatial resolution of nuclear medicine imaging, it is not possible to separate the peri-infarct zone from the central area of necrosis, except in the cases of extremely large infarctions e.g., the "donut" sign.

Proton magnetic resonance imaging was first shown to be feasible by Lauterbur in 1973. The intensity of the radio frequency signals received from different tissues is affected by the distribution of protons in tissue and also by their relaxation times (T-1, T-2), which are in turn influenced by the local chemical environment and motion of molecules. Since water is the major constituent of most tissues, the magnetic resonance image intensity is largely controlled by the protons in water. Certain substances which are said to have paramagnetic properties can modify these relaxation times and change the appearance of the images.

Magnetic resonance imaging has been shown to be particularly suited for imaging of the cardiovascular system. Since rapidly flowing blood produces no magnetic resonance signal, there is a natural contrast between the blood and surrounding vascular and cardiac structures. By synchronizing the image acquisition to the electrocardiographic cycle (cardiac gating) the effects of cardiac motion can be minimized and high resolution images of the ventricular walls can be obtained. Lanzer et al., *Radiology* 150: 121 (1984); 155: 681–686 (1985).

Early studies performed in animal hearts ex situ without gating showed that acutely infarcted myocardium exhibit increased signal intensity relative to normal tissue. Direct measurements both in excised and bearing hearts have shown that the T-1 and T-2 relaxation times of acutely infarcted cardiac muscle are prolonged. This increase in T-1 and T-2 in infarcted muscle is a nonspecific finding related to a localized increase in tissue water from edema. Wesby et al, *Circulation* 69: 125 (1984); Frank et al, *Clin Res.* 17: 217A (1976) (abstract).

Following the early animal studies without ECG gating, additional studies demonstrated in man that acute myocardial infarction could be recognized as an area of increased magnetic resonance signal intensity with the use of ECG gating. Pohost et al., *Circulation* 66 (Supl II): II-39 (1982).

Most recently, studies have shown that the presence of a localized area of increased magnetic resonance signal intensity within the myocardium is not a specific finding for acute myocardial infarction, as this effect may be present in as many as 83% of asymptomatic normal volunteers. These recent studies have emphasized the need for a tissue-specific paramagnetic contrast agent which will localize only in areas of acute myocardial infarction.

Gd-DTPA (gadolinium ion chelated with the ligand diethylenetriaminepentaacetic acid) has been proposed as a paramagnetic contrast agent. Wesby et al., *Radiology* 153: 165–169 (1984); McNamara et al, *Radiology* 153: 157–163 (1984). This agent, which causes differential changes in T-1 and T-2 in tissues based upon differences in blood flow, has been shown to be helpful for identifying areas of infarct (no blood flow) from areas of intact perfusion. However, Gd-DTPA has no tissue specificity. It does not localize in the peri-infarction tissue.

While magnetic resonance imaging provides improved spatial resolution over nuclear imaging, there is presently no technique available for tissue-specific magnetic resonance imaging which would permit definition of an area of tissue calcification, in particular, the peri-infarct zone of an acute myocardial infarction. What is needed is a paramagnetic contrast agent which would permit precise localization and sizing of the infarct and peri-infarct zone.

SUMMARY OF THE INVENTION

According to the present invention, nuclear magnetic resonance imaging of human or animal tissue is improved by administering an effective amount of a paramagnetic pyrophosphate compound as a contrast agent. Improved imaging of cardiac tissue, in particular, is possible. The contrast agent is most effectively administered in intravenously in solution with a physiologically acceptable carrier. An effective dosage for intraveneous administration is about 30 to about 325 mg per kilogram of body weight. When ferric pyrophosphate is used as the contrast agent, this dosage effectively results in an optimum localized tissue concentration of about 0.06 mg Fe(III) as pyrophosphate per gram of tissue within one hour of administration.

DETAILED DESCRIPTION OF THE INVENTION

The use of a paramagnetic pyrophosphate compound as a contrast agent makes possible the localization and sizing of tissue calcification. In particular, these agents permit the localization and sizing of acute myocardial infarctions, and visualization of the peri-infarct zone.

Pyrophosphate binds to sites of intracellular and extracellular calcification in human and animal tissues. Enhanced magnetic resonance imaging is possible, for example, of any site where there has been tissue necrosis resulting in calcification.

Paramagnetic atomic species have an odd number of electrons and a partially-filled outer shell, such as is found in the transition elements, and those elements of the lanthanide and actinide series. The paramagnetic pyrophosphate compound utilized in the present invention is a pyrophosphate complex of a paramagnetic species. Such paramagnetic species include, for example, manganese (II), copper (II), cobalt (II), manganese (III), copper (III), cobalt (III), chromium (II), chromium (III), nickel (II), nickel (III), gadolinum (III), iron (II) and iron (III). The preferred contrast agent is ferric pyrophosphate ($Fe_4(P_2O_7)_3 \cdot x\ H_2O$), also known as iron (III) pyrophosphate.

Adequate tissue concentrations of stable paramagnetic pyrophosphate compound can be obtained to induce paramagnetic enhancement and precise contrast enhancement of acute myocardial infarctions. Magnetic resonance images are generated by any suitable magnetic resonance imaging device, such as a Fonar Beta-3000M Magnetic Redonance Imaging System. Preferably, the device is coupled to an electrocardiogram device for cardiac gating. Fifteen-minute images are acquired serially over an approximately one hour time span. The paramagnetic pyrophosphate compound, which has localized in the area of the infarction, will increase the signal intensity and appear as a bright spot in the resulting images. Optimum infarct resolution will generally occur between 30–45 minutes after injection of the contrast agent. Because of the excellent anatomic resolution of magnetic resonance imaging, both the size and location of the infarct will be identified as enhancement of the signal around the central infarct.

Since soft tissue calcification results from injury to tissues elsewhere in the body, the invention can also be used to enhance NMR imaging of calcium deposition outside the heart. In addition to sites of intracellular and extracellular calcification in other tissues of the body such as skeletal muscle and intracerebral infarcts (stroke), areas of heterotopic calcification, such as is caused by myositis ossificans, may be imaged It is known that pyrophosphate will bind the proteinaceous substance amyloid, which accumulates in certain tissues during disease. A paramagnetic pyrophosphate compound can be used as a contrast agent for magnetic resonance imaging of amyloid deposition in organs such as kidneys, heart and brain, for example.

The contrast agent may be administered in the form of a physiologically acceptable solution of a paramagnetic pyrophosphate compound. An effective dosage is about 30 to about 325 mg of paramagnetic pyrophosphate compound per kilogram of body weight.

According to one embodiment of the invention, ferric pyrophosphate in the form of water-soluble crystals is dissolved in sterile aqueous sodium chloride. Specifically, 7.3 grams of ferric pyrophosphate in water-soluble crystalline form containing 10.5–12.5% iron by weight is vortexed in 0.9% sterile aqueous sodium chloride until dissolution is complete. The final green-colored solution is then diluted with 0.9% sterile aqueous sodium chloride to a volume of 30 ml for intravenous administration.

It was determined that maximum image enhancement occurs when the localized tissue concentration of ferric pyrophosphate is sufficient to provide a local tissue concentration of ferric ion on the order of 0.06 mg Fe(III) as pyrophosphate per gram of tissue. Since blood flow will vary depending on the degree of ischemia in the heart, the time to optimum utilization of the contrast agent in cardiac imaging can very. The best results are obtained from administration of a single bolus intravenous injection, followed by serial imaging over the course of approximately one hour. During this time period, one of the sets of serial images will show peak contrast enhancement.

Magnetic resonance images may be obtained from any suitable magnetic resonance imaging device. One such device commonly available is the Fonar Beta-3000M Magnetic Resonance Imaging System. The magnetic element in this system is a hybrid magnet which utilizes both permanent and resistive magnetization. The field strength is 0.3 Tesla +/- 10%, with a magnetic field uniformity of 6 parts per million RMS variation over a 30 centimeter sphere. The radio frequency transmitter which transmits the RF pulse sequence uses a saddle coil with a peak RF output of 500 watts with a typical watt power input to the RF coil for a spin echo pulse sequence of 60 milliseconds per slice. The radio frequency receiver coil is of the "whole body" type which uses a 55.9 centimeter by 32.4 centimeter circular configuration.

Other magnetic resonance imaging systems known to those skilled in the art may be utilized.

It is desirable to eliminate the effect of the motion of the beating heart during magnetic resonance cardiac imaging. Thus, cardiac imaging is preferably connected with electrocardiagraphic gating. This is accomplished by connecting the subject being imaged to a standard electrocardiograph machine to obtain an electrical output signal of the subject's R wave, which indicates the beginning of ventricular depolarization. The R wave is used to trigger emission of a spin-echo pulse sequence from the imaging system.

The repetition time (TR) is typically defined as the period of time between the beginning of a pulse sequence and the beginning of a succeeding pulse sequence at the same slice level. The TR is preferably chosen to be 300 milliseconds less than the measured R-R interval to insure that the imaging sequence will be completed within one cardiac cycle (ventricular systole and diastole).

Spin-echo imaging is preferred, with a short echo delay time (TE) of about 28 milliseconds.

The following study using $^{59}$Fe(III) Pyrophosphate and Tc-99m pyrophosphate confirms that the two forms of pyrophosphate have the same biodistribution.

Comparison of Tissue Distribution of Tc-99m Pyrophosphate and $^{59}$Fe(III) pyrophosphate Pigs were surgically thorocotomized with exposure of the left anterior descending coronary artery. The artery was then ligated at its midpoint in order to create an acute anterior wall myocardial infarction. Forty-eight hours following surgery the animals were injected with one hundred microcuries of $^{59}$Fe-ferric pyrophosphate. One hundred microcuries of $^{59}$Fe-ferric chloride (ICN Chemical and Radioisotope Division, Irvine, CA) as a solution in 1.0 N HCl was added to a solution of 50 mg sodium pyrophosphate in 1 ml of 0.01 N NCl. Formation of $^{49}$Fe-ferric pyrophosphate was confirmed by spotting an aliquot of the preparation on Instant Thin Layer Media (Gelman Inst. Co., Ann Arbor, MI) and developing the strip with 85% methanol. Under these conditions, $^{59}$Fe-ferric chloride migrates with the solvent front and $^{59}$Fe-ferric pyrophosphate remains at the origin. Then the radioactive solution and an additional nonradioactive ferric pyrophosphate solution were mixed (7.3 g ferric pyrophosphate crystals containing 10.5–12.5 wt % Fe in 30 ml 0.9% NaCl) to make a 4 ml solution for injection into the experimental animals.

Before each experimental animal was injected with $^{59}$Fe(III) pyrophosphate, a small aliquot ("standard") of the dose was saved and weighed. The syringe containing the dose was also weighed before and after injecting the animal, so that the weight of the injected dose could be determined. The amount of radioactivity administered to the animal ("counts in dose") is then calculated by counting the standard:

$$\text{Counts in dose} = \text{counts in standard} \times \frac{\text{weight of injected dose}}{\text{weight of standard}}$$

In a similar manner a 10 mCi dose of Tc-99m pyrophosphate was prepared for intraveneous injection and a "standard" of the dose was saved and weighed.

Forty-eight hours following creation of the infarct, the animals were injected with both Tc-99m pyrophosphate and $^{59}$Fe ferric pyrophosphate.

One hour following injection of the two different radiolabeled forms of pyrophosphate, the animals were sacrificed. At the time of sacrifice, tissue samples were taken from the normal and infarcted areas of the myocardium of each animal. These samples were weighed and then counted in two energy windows for techneti-um-99m and $^{59}$Fe content. The radioactivity in each tissue sample could be expressed as a percentage of the injected dose per gram of tissue:

$$\frac{\text{\% of injected dose}}{\text{gram tissue}} = \frac{\text{counts in sample}}{\text{weight of spl.} \times \text{injected dose}} \times 100$$

It was assumed that $^{59}$Fe has the same biodistribution as nonradioactive iron. The concentration of ferric pyrophosphate in the tissue was then determined from the % of injected dose of $^{59}$Fe per gram of tissue:

$$\frac{\text{\#mmol Fe—Pyrophosphate}}{\text{gram tissue}} = \frac{\text{\% of injected dose}}{\text{gram tissue}} \times \frac{\text{mmol Fe—Pyrophosphate-injected}}{100}$$

At autopsy, tissue samples were obtained from the central region of the anatomic area of infarction, the periphery of the infarct, and the posterior wall of the left ventricle in an area of normal appearing tissue remote from the area of infarction. The results of this study are shown in Table I.

TABLE 1

Comparison of $^{59}$Fe(III) Pyrophosphate and Tc-99 m Pyrophosphate Biodistribution

| | Tc-99 m Pyrophosphate (% dose/gm) | | | $^{59}$Fe(III) Pyrophosphate (% dose/gm) | | |
|---|---|---|---|---|---|---|
| | Center | Edge | Normal | Center | Edge | Normal |
| 1. | .0057 | .0064 | .0024 | .0072 | .0085 | .0063 |
| 2. | .0096 | .0139 | .0025 | .0089 | .0125 | .0076 |
| 3. | .0044 | .0057 | .0021 | .0056 | .0068 | .0040 |
| 4. | .0065 | .0101 | .0030 | .0066 | .0132 | .0036 |
| Average | .0066 | .0092 | .0028 | .0071 | .0102 | .0054 |
| Ratio/N1 | 2.4 | 3.3 | | 1.3 | 1.9 | |
| Ratio/Center | | 1.4 | | | 1.5 | |

The data confirms that iron(III) pyrophosphate has the same tissue distribution in infarcted and noninfarcted tissue as Tc-99m pyrophosphate. Enhanced localization in the edge (peri-infarction area) of the infarct was apparent for both pyrophosphates. The extent of this localization ("Ratio/center") was similar: iron(III) pyrophosphate, 1.5; Tc-99m pyrophosphate, 1.4.

The practice of the present invention is illustrated on laboratory animals as follows.

In vivo Enhancement of Magnetic Resonance Signal Intensity By Ferric Pyrophosphate Anterior wall myocardial infarctions were surgically created by ligating the left anterior descending coronary artery of four pigs. Forty-eight hours following ligation, the animals were injected intravenously with 20 ml of a ferric prophosphate solution (7.3g Fe(III) pyrophosphate (Dr. Paul Lohmann, Chemische Fabrik GmbH, Emmenthal, Germany) containing 10.5–12.5 wt % Fe dissolved in 30 ml 0.9% NaCl). Using ECG gating and a spin echo pulse sequence with a TE of 28 milliseconds and a TR which varied from 200 to 500 milliseconds based on the animal's heart rate, serial magnetic resonance images were obtained at 15 minutes, 30 minutes, and 45 minutes after injection. These were compared to a baseline study obtained prior to the injection of the paramagnetic agent. Peak enhancement of the area of myocardial infarction which was initially seen only as a vague area of increased signal intensity in the noncontrast enhanced studies was observed in 3 animals during the second (15 minute) study and in 1 animal in the 30 minute study. Quantification of the enhancement of signal intensity is exhibited in Table II. The infarct showed an average of 52% enhancement compared to the normal myocardium. This enhancement was confirmed in visual assessment of the images.

TABLE II

Paramagnetic Signal Enhancement
In Gated Magnetic Resonance Imaging

| Scan Time (min) | Signal Intensity (infarct/normal muscle) | | | |
|---|---|---|---|---|
| | 1 | 2 | 3 | 4 |
| 0–15 | 1.66 | 1.18 | 1.32 | 1.08 |
| 15–30 | 1.71(21%)* | 1.62(37%)* | 2.88(118%)* | 1.11 |
| 30–45 | 1.70 | 1.05 | 1.18 | 1.42(31%)* |
| 45–60 | 1.43 | | | 0.88 |

*Maximal % increase

The time to peak enhancement following bolus administration of a large quantity of ferric pyrophosphate varies. There is apparently a well-defined range of ferric pyrophosphate tissue concentrations over which signal enhancement will occur.

As tissue concentrations in the area of infarct are rising, there will be a short time period during which the paramagnetic pyrophosphate concentration is optimum for signal enhancement. For ferric pyrophosphate, the calculated optimum in enhancement occurs at tissue concentrations on the order of about 0.06 mg Fe(III) as pyrophosphate/gram of tissue. An intraveneous injection of a quantity of ferric pyrophosphate large enough to reach this tissue concentration is therefore preferable to ensure optimum contrast. A dosage of about 30 to about 325 mg of ferric pyrophosphate per kilogram of body weight is effective for reaching this tissue concentration.

The present invention may be embodied in other specific forms without departing from the spirit or essential attributes thereof and, accordingly, reference should be made to the appended claims, rather than to the foregoing specification, as indicating the scope of the invention.

We claim:

1. A method for nuclear magnetic resonance imaging of calcium deposits in human or animal tissue comprising administering an amount of a solution of a paramagnetic pyrophosphate compound as a contrast agent effective to enhance the nuclear magnetic resonance image of said calcium deposits, and obtaining nuclear magnetic resonance images of said calcium deposits.

2. A method according to claim 1 wherein the imaged tissue comprises cardiac tissue.

3. The method according to claim 1 wherein the paramagnetic pyrophosphate compound is administered intraveneously.

4. The method according to claim 3 wherein the dosage of paramagnetic pyrophosphate compound is between about 30 and about 325 mg per kg of body weight.

5. A method according to claim 1 wherein the paramagnetic pyrophosphate compound is ferric pyrophosphate.

6. A method according to claim 1 wherein the paramagnetic pyrophosphate is gadolinium (III) pyrophosphate.

7. The method according to claim 5 wherein the tissue concentration of Fe(III) as ferric pyrophosphate in the tissue being imaged reaches about 0.06 mg per gram of tissue.

8. A method according to claim 7 wherein said Fe(III) tissue concentration as ferric pyrophosphate is achieved within one hour after intraveneous administration of ferric pyrophosphate.

9. A method for nuclear magnetic resonance imaging of calcium deposits in a myocardial infarction comprising administering an amount of a solution of a paramagnetic pyrophosphate compound as a contrast agent effective to enhance the nuclear magnetic resonance image of said calcium deposits, and obtaining nuclear magnetic resonance images of said calcium deposits.

10. The method according to claim 9 wherein the paramagnetic pyrophosphate compound is administered intravenously 11. A method according to claim 10 wherein the perinfarct zone is imaged.

12. The method according to claim 10 wherein the dosage of paramagnetic pyrophosphate compound is between about 30 and about 325 mg per kg of body weight.

13. The method according to claim 9 wherein the paramagnetic pyrophosphate compound is ferric pyrophosphate.

14. The method according to claim 13 wherein the tissue concentration of Fe(III) as ferric pyrophosphate in the tissue being imaged reaches about 0.06 mg per gram of tissue.

15. A method according to claim 14 wherein said Fe(III) tissue concentration is achieved within one hour after intravenous administration of ferric pyrophosphate.

16. The method according to claim 9 wherein the paramagnetic pyrophosphate compound is gadolinium (III) pyrophosphate.

17. A method for nuclear magnetic resonance imaging of calcium deposits in an acute myocardial infarction comprising intravenously administering a solution containing from about 30 mg to about 325 mg of ferric pyrophosphate per kg of body weight as a contrast agent to enhance the nuclear magnetic resonance image of said calcium deposits, and obtaining nuclear magnetic resonance images of said calcium deposits.

18. A method for nuclear magnetic resonance imaging of amyloid deposits in human or animal organs or tissue comprising administering an amount of a solution of a paramagnetic pyrophosphate compound as a contrast agent effective to enhance the nuclear magnetic resonance image of said amyloid deposits, and obtaining nuclear magnetic resonance images of said amyloid deposits.

* * * * *